United States Patent
Beller et al.

(10) Patent No.: US 6,686,495 B2
(45) Date of Patent: Feb. 3, 2004

(54) PROCESS FOR THE PREPARATION OF MONO-, BI- OR POLY-FUNCTIONAL BIARYLS

(75) Inventors: Matthias Beller, Rostock (DE); Mario Gómez-Andreu, Rostock (DE); Alexander Zapf, Rostock (DE); Ralf Karch, Kleinostheim (DE); Ingo Kleinwächter, Hanau (DE); Oliver Briel, Offenbach (DE)

(73) Assignee: OMG AG & Co KG, Hanau-Wolfgang (DE)

( * ) Notice: Subject to any disclaimer, the term of this patent is extended or adjusted under 35 U.S.C. 154(b) by 0 days.

(21) Appl. No.: 09/977,253

(22) Filed: Oct. 16, 2001

(65) Prior Publication Data

US 2002/0107426 A1 Aug. 8, 2002

(30) Foreign Application Priority Data

Oct. 17, 2000 (DE) .......................................... 100 51 316

(51) Int. Cl.$^7$ .......................... C07C 2/66; C07C 255/50
(52) U.S. Cl. .................. 558/411; 558/431; 585/457
(58) Field of Search .......................... 585/457; 558/411, 558/431; 570/127, 206, 209; 568/630, 634, 56, 609, 610; 564/307, 457; 544/245, 338; 546/152, 251; 548/217, 343.5, 469; 549/469, 456, 41

(56) References Cited

U.S. PATENT DOCUMENTS 6,316,380 B1   11/2001   Nolan et al.
6,369,265 B1   4/2002    Nolan et al.
6,402,802 B1   6/2002    Nolan et al.
6,403,801 B1   6/2002    Nolan et al.

FOREIGN PATENT DOCUMENTS

| DE | 3842622 C1  | 4/1990 |
| DE | 3941494 A1  | 6/1990 |
| DE | 4236103 A1  | 4/1994 |
| DE | 19651439 A1 | 6/1998 |
| DE | 69703543 T2 | 5/2001 |

OTHER PUBLICATIONS

Xiaohong Bei, et al. "Palladium/P, O–Ligand–Catalyzed Suzuki Cross–Coupling Reactions of Arylboronic Acids and Aryl Chlorides. Isolation and Structural Characterization of (P,O)–Pd(dba) Complex," J. Org. Chem, 1999, 64, pp. 6797–6803.

Primary Examiner—Joseph K. McKane
Assistant Examiner—Ebenezer Sackey
(74) Attorney, Agent, or Firm—Kalow & Springut LLP

(57) ABSTRACT

A process for the preparation of mono-, bi- or poly-functional biaryls in the presence of a metal complex of the general formula IV

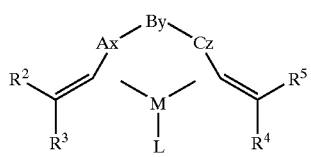

(IV)

as catalyst.

35 Claims, No Drawings

PROCESS FOR THE PREPARATION OF MONO-, BI- OR POLY-FUNCTIONAL BIARYLS

INTRODUCTION AND BACKGROUND

The present invention relates to a process for the preparation of biaryls using active nickel, palladium or platinum catalysts.

Biaryl compounds, especially biphenyl compounds, are of commercial importance as fine chemicals, intermediates for pharmaceuticals, optical brightening agents and agrochemicals.

A frequently used method of synthesising biaryls is the Suzuki reaction, in which iodo- or bromo-aromatic compounds as well as aryl triflates and, more rarely, chloroaromatic compounds are reacted with aryl-, vinyl- or alkylboronic acid derivatives in the presence of palladium catalysts. An overview article describing this method is, for example, M. Beller, C. Bolm, Transition Metals for Organic Synthesis, Vol. 1, p. 208, VCH-Wiley, Weinheim 1998.

Suitable catalysts for use within the scope of the Suzuki reaction are generally palladium and nickel compounds. Despite the economic advantage of nickel catalysts, palladium catalysts are preferred over nickel catalysts because of their lower toxicity and their greater tolerance towards functional groups. In the case of the use of palladium catalysts, both palladium(II) and palladium(0) complexes are used in Suzuki reactions. According to the literature, there are formulated as the active catalytic species coordinatively unsaturated 14-and 16-electron palladium(0) species, which are stabilized with donor ligands such as phosphanes. In particular when more inexpensive educts such as aryl bromides or aryl chlorides are used, the addition of stabilizing ligands is required in order to achieve adequate catalytic activation of the starting materials.

The catalyst systems described for Suzuki reactions frequently exhibit satisfactory catalytic turnover numbers (TON) only with uneconomical starting materials such as iodoaromatic compounds and activated bromoaromatic compounds. Otherwise, in the case of deactivated bromoaromatic compounds (i.e. bromoaromatic compounds having "electron-displacing" substituents or sterically hindered bromoaromatic compounds), and especially in the case of chloroaromatic compounds, large amounts of catalyst—normally over 1 mol. %—must be added in order to achieve commercially usable turnovers.

In addition, because of the complexity of the reaction mixtures, simple catalyst recycling is impossible, so that catalyst costs generally also stand in the way of commercial realization. Although catalyst systems based on water-soluble phosphanes give satisfactory catalyst activities for the industrially important reaction of 2-chlorobenzonitrile with p-tolylboronic acid, the catalysts contain expensive sulfonated phosphanes. Moreover, a number of chloroaromatic compounds cannot as yet be activated in a commercially satisfactory manner even with those catalysts.

More recent active catalyst systems are based on cyclopalladated phosphanes (W. A. Herrmann, C. Broβmer, K. Öfele, C. -P. Reisinger, T. Priermeier, M. Beller, H. Fischer, Angew. Chem. 1995, 107, 1989; Angew. Chem. Int. Ed. Engl. 1995, 34, 1844) or mixtures of sterically demanding arylphosphanes (J. P. Wolfe, S. L. Buchwald, Angew. Chem. 1999, 111, 2570; Angew. Chem. Int. Ed. Engl. 1999, 38, 2413) or tri-tert.-butylphosphane (A. F. Littke, G. C. Fu, Angew. Chem. 1998, 110, 3586; Angew. Chem. Int. Ed. Engl. 1998, 37, 3387) with palladium salts or palladium complexes.

However, inexpensive chloroaromatic compounds cannot generally be activated in a commercially satisfactory manner with those catalysts either, since the catalyst productivities (TON) are below 10,000 and the catalyst activities (TOF) are below 1000 h$^{-1}$. Accordingly, in order to achieve high yields in particular in the case of such industrially valuable starting materials, it is necessary to use comparatively large and hence very expensive amounts of catalyst. For example, the catalyst costs for the preparation of one kilogram of an organic intermediate having a molecular weight of 200 using 1 mol. % palladium catalyst are more than 100 US$ at current noble metal prices, which shows the necessity of improving catalyst productivity. Accordingly, despite all the further developments made to catalysts in recent years, only a small number of industrial reactions of the arylation of chloroaromatic compounds have become known to date.

For the reasons mentioned, there is a great need for new processes for the preparation of biaryls, which processes do not exhibit the disadvantages of the known catalytic processes, and for palladium catalyst systems suitable therefor which contain inexpensive ligands, which are suitable for implementation on an industrial scale and which yield the biaryls in a high yield, with high catalyst productivity and in high purity.

SUMMARY OF THE INVENTION

That object can be achieved by a process for the preparation of mono-, bi- or poly-functional biaryls of the general formula I $$\text{Ar—Ar'} \tag{I}$$

by reaction of an aryl compound of formula II $$\text{Ar—X} \tag{II}$$

with an arylboronic acid derivative of formula III $$\text{Ar'—B(OR}^1)_2 \tag{III}$$

in the presence of a catalyst, which process is characterised in that the catalyst used is a metal complex of the general formula IV

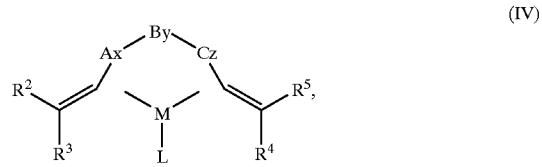

wherein in formulae I to IV

Ar and Ar' each independently of the other represents mono- or poly-cyclic aromatic that is optionally substituted as desired and has up to 14 carbon atoms in the ring, or heteroaromatic that is optionally substituted as desired and has from 5 to 10 atoms in the ring, of which up to four atoms independently of one another may be N, O or S, X represents I, Br, Cl, OSO$_2$CF$_3$, OSO$_2$(aryl), OSO$_2$ (alkyl), N$_2^+$, M represents nickel, palladium or platinum, L represents a monodentate phosphoroorganic ligand PR$^6$R$^7$R$^8$, A, B, C each independently of the others represents oxygen, sulfur, CH$_2$, C(R$^9$)$_a$(R$^{10}$)$_b$, N(R$^{11}$)$_c$, Si(R$^{12}$)$_d$(R$^{13}$)$_e$, wherein a, b, c, d, e may each independently of the others be 0 or 1, and when a, b, c, d, e of at least one of the radicals in question is 0, A, B and C may also be part of a ring system, x, y, z represent 0 or 1 and x+y+z=from 1 to 3, $R^1$ represents hydrogen, alkyl, aryl or alkenyl, wherein in formula III $B(OR^1)_2$ may also form a ring system, $R^6$ to $R^8$ have the meanings of $R^1$, or represent O-alkyl, O—C(O)-alkyl, O-(aryl), as well as groups of any desired condensed ring system, $R^2$ to $R^5$.

and $R^9$ to $R^{13}$ have the meanings of $R^1$, or represent O-alkyl, O—C(O)-alkyl, O-(aryl), O—C(O)-aryl, F, Cl, OH, $NO_2$, Si (alkyl)$_3$, $CF_3$, CN, $CO_2H$, C(O)H, $SO_3H$, $NH_2$, NH(alkyl), N(alkyl)$_2$, P(alkyl)$_2$, $SO_2$(alkyl), SO(alkyl), SO(aryl), $SO_2$(aryl), $SO_3$ (alkyl), $SO_3$(aryl), S-alkyl, S-aryl, S-alkenyl, NH—CO(alkyl), $CO_2$(alkyl), $CONH_2$, CO(alkyl), NHCOH, $NHCO_2$(alkyl), CO(aryl), $CO_2$(aryl), CH=CH—$CO_2$(alkyl), CH=CH—$CO_2$H, P(aryl)$_2$, PO(aryl)$_2$, PO(alkyl)$_2$, $PO_3H$, PO(O-alkyl)$_2$, and groups of any desired condensed ring system, wherein alkyl represents hydrocarbon radical having from 1 to 10 carbon atoms and alkenyl represents mono- or poly-unsaturated hydrocarbon having from 1 to 10 carbon atoms, each of which may be branched and/or substituted by Cl, F, alkyl, O-alkyl, phenyl, O-phenyl, and aryl represents an optionally Cl-, F-, alkyl-, O-alkyl-, phenyl-, O-phenyl-substituted aromatic or heteroaromatic having from 5 to 10 atoms in the ring.

In the process according to the invention, aryl compounds of formula II are preferably reacted with arylboronic acid derivatives of formula III in which Ar and Ar' each independently of the other represents an optionally substituted phenyl, naphthyl, anthryl, phenanthryl or biphenyl.

In the process according to the invention, the aryl compounds used are preferably compounds of formula IIa

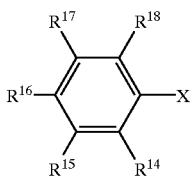

(IIa)

wherein $R^{14}$ to $R^{18}$ have the meanings given for $R^2$ to $R^5$ and $R^9$ to $R^{13}$, and the arylboronic acid derivatives used are preferably compounds of formula IIIa

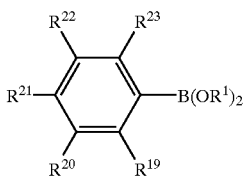

(IIIa)

wherein $R^{19}$ to $R^{23}$ have the meanings given for $R^2$ to $R^5$ and $R^9$ to $R^{13}$.

There are used as the catalyst in the process according to the invention especially metal complexes of formula IV that contain as the metal M preferably nickel and palladium, and especially palladium.

In the catalysts of formula IV, the diene component is particularly preferably diallyl ether, diallylamine, diallylmethylamine, N-acetyldiallylamine, diallyl sulfide, diallylsilane, diallyldimethylsilane, divinyldisiloxane, bis-([2]thienylmethyl) ether, bis-(2-cyano-3ξξ-[2]furyl-allyl) ether, 1,1,3,3-tetramethyl-1,3-divinyldisiloxane, difurfuryl ether, difurfurylamine, bis(thiophen-2-yl-methyl)-amine, difurfuryl sulfide, 1,1,3,3-tetramethyl-1,3-dithien-2-yl-disiloxane, 1,1,3,3-tetramethoxy-1,3-divinyl-disiloxane, 1,3-dimethyl-1,3-divinyldisiloxanediol, 1,3,5,7-tetramethyl-1,3,5,7-tetravinylcyclotetra-siloxane, 1,3,5-trimethyl-1,3,5-trivinyl-cyclotrisiloxane, 1,3,5,7,9-pentamethyl-1,3,5,7,9-pentavinyl-cyclopentasiloxane, 1,3-divinylbenzene, 2,6-divinylpyridine and derivatives thereof.

The ligands L in the catalysts of formula IV are preferably trialkylphosphines and triarylphosphines. Special preference is given to tricyclohexylphosphine, tri-n-butylphosphine, tri-tert-butylphosphine, triphenylphosphine, tri-o-tolylphosphine, di-(1-adamantyl)-n-butylphosphine, di-(1-adamantyl)-isopropyl-phosphine, di-(1-adamantyl)-cyclohexylphosphine, 2-(dicyclohexylphosphino)biphenyl, 2-(dicyclohexylphosphino)toluene, N,N-dimethyl-2-(dicyclohexylphosphino)aniline, 2-(di-tert-butylphosphino) biphenyl, 2-(di-tert-butylphosphino)toluene, N,N-dimethyl-2-(di-tert-butylphosphino)aniline.

DETAILED DESCRIPTION OF INVENTION

The process according to the invention is especially suitable for the synthesis of biaryls of formula I wherein aryl and aryl' represent a substituted phenyl, naphthyl, anthryl, phenanthryl, biphenyl radical or/and a five-, six- or seven-membered heteroaromatic radical optionally having nitrogen, oxygen or sulfur atoms in the ring. In the case of the heteroaromatic radicals, substituted pyridines, pyrimidines, oxazoles, imidazoles, pyrazines, quinolines, indoles, furans, benzofurans or/and thiophenes are particularly preferred.

The process according to the invention has proved especially suitable for the preparation of compounds of formula I wherein aryl and aryl' carry up to 4 substituents which may independently of one another be alkyl, O-alkyl, O—CO-alkyl, N-alkyl$_2$, phenyl, aryl, fluorine, chlorine, $NO_2$, CN, COOH, CHO, $SO_2$-alkyl, NH-alkyl, COO-alkyl, $CONH_2$, CONH-alkyl, CO-alkyl, CO-phenyl and PO-phenyl$_2$, wherein alkyl and aryl are as defined above.

In the process according to the invention, the catalyst is used in an amount of from 0.001 to 10 mol. % and preferably from 0.01 to 1 mol. %, based on the concentration of aryl compound or arylboronic acid derivative.

The process is normally carried out in a solvent. There are used as the solvent generally inert organic solvents and/or water. Especially suitable as solvents or solvent mixtures are water, aliphatic ethers, aromatic or aliphatic hydrocarbons, alcohols and esters. Examples of those especially suitable solvents are THF (tetrahydrofuran), dioxane, diethyl ether, diglyme (diethylene glycol dimethyl ether), MTBE (methyl tert-butyl ether), DME (ethylene glycol dimethyl ether), toluene, xylenes, anisole, ethyl acetate, methanol, ethanol, butanol, ethylene glycol, ethylene carbonate and propylene carbonate. However, dipolar aprotic solvents are also suitable, such as dialkylsulfoxides, nitrites, N,N-dialkylamides of aliphatic carboxylic acids or alkylated lactams. Examples thereof which may be mentioned are dimethylsulfoxide, acetonitrile, benzonitrile, N,N-dimethylacetamide, N,N-dimethylformamide and N-methylpyrrolidone.

The process is preferably carried out at temperatures of from 0 to 200° C.; in many cases it has proved expedient to work at temperatures of from 40 to 180° C., preferably at from 60 to 160° C. The reaction can be carried out at a pressure of from 0.5 to 100 bar, with a pressure in the range from normal pressure to 60 bar preferably being used.

It is advantageous to carry out the reaction in the presence of a base. Suitable therefor are primary, secondary or tertiary amines, such as alkylamines, dialkylamines, trialkylamines, which may be alicyclic or open-chained. There come into consideration as bases also alkali metal or alkaline earth metal salts of aliphatic or aromatic carboxylic acids, especially acetates, propionates, benzoates, or alkali metal or alkaline earth metal carbonates, hydrogen carbonates, phosphates, hydrogen phosphates, oxides or hydroxides.

It is also possible to use as bases in the process according to the invention metal alkoxides, especially alkali metal or alkaline earth metal alkoxides, such as sodium methanolate, potassium methanolate, sodium ethanolate, potassium ethanolate, magnesium methanolate, magnesium ethanolate, calcium ethanolate, calcium methanolate, sodium tert-butanolate or potassium tert-butanolate.

The base can have a positive effect on the progress of the reaction by activating the arylboronic acid to anionic boranate species. In addition to the above-mentioned bases, such an activation can also be achieved by the addition of fluoride salts such as, for example, caesium fluoride, calcium fluoride, sodium fluoride, potassium fluoride, tetraalkylammonium fluorides.

The base is advantageously used in an amount of from 0.1 to 5 mol.-equivalent, based on the concentration of aryl compound or arylboronic acid derivative.

The catalysts of formula IV that are used may either be employed in the form of molecularly defined compounds or prepared in situ by reaction of a metal diene precursor with a corresponding phosphoroorganic compound $PR^6R^7R^8$. A catalyst precursor is, for example, a complex compound between the metal in oxidation stage 0 and one or more diene ligands $R^2R^3C=CH-A_x-B_y-C_z-CH=CR^4R^5$. Typical catalyst precursors are, for example, complexes of Pd(0) or Ni(0) with such dienes, it being possible for those dienes to coordinate in the catalyst precursor in both a monodentate and a bidentate manner.

It is a particular advantage of the catalyst systems to be used in the process according to the invention that preforming, that is to say the preliminary reaction to the active catalyst, is particularly simple to carry out, and that it is possible to work with a metal diene/phosphoroorganic compound ratio of 1:1. As a result, an excess of expensive phosphoroorganic ligands is avoided, working up is simpler, and more active catalysts are obtained.

When using chloroaromatic compounds, bromoaromatic compounds, aryl triflates or aryl mesylates and related starting materials, it is sometimes advantageous to add a co-catalyst to the catalyst. The co-catalyst may be a salt of a halogen, especially a halide of the alkali metal elements or alkaline earth metal elements, an ammonium halide, a tetraalkylammonium halide, a phosphonium halide and/or a tetraalkylphosphonium halide. The co-catalyst is preferably a fluoride, bromide or chloride. Special preference is given to calcium fluoride, tetrabutylammonium fluoride, caesium fluoride, potassium fluoride, sodium fluoride, lithium bromide, sodium bromide, potassium bromide, caesium bromide, lithium chloride, tetrabutylammonium chloride, tetrabutylammonium bromide, benzyltrimethylammonium bromide, benzyltrimethylammonium chloride, trioctylmethylammonium bromide, tetraphenylphosphonium bromide, tetraphenylphosphonium chloride.

The co-catalyst is used in an amount of from 0.01 to 500 mol. % and preferably from 0.1 to 300 mol. %, based on the amount of aryl compound or arylboronic acid derivative. Where it is advantageous in terms of the process, the reaction can also be carried out in the co-catalyst as solvent (salt melt).

With the process according to the invention it is possible to achieve turnover values of the catalysts of the order of 1,000,000 and above for bromoaromatic compounds as starting materials, and 10,000 and above for chloroaromatic compounds.

Accordingly, because of the catalyst activities, it is possible in the process according to the invention to use extremely small amounts of catalyst, so that the catalyst costs, especially where palladium catalysts are used, are not cost-limiting in comparison with conventional Suzuki reactions for the corresponding process.

The biaryls prepared according to the invention can be used commercially, for example as intermediates for pharmaceuticals (for example for AT II antagonists) and agrochemicals, as ligand precursors for metallocene catalysts, as optical brightening agents and structural units for polymers.

EXAMPLES

General Working Specification

In a pressure tube, under an argon atmosphere, 3.0 mmol. of aryl halide, 4.0 mmol. of phenylboronic acid, 3.0 mmol. of tripotassium phosphate, 3.0 mmol. of potassium fluoride, a corresponding amount of Pd(0) catalyst and 100 µl of hexadecane (as internal standard for the GC analysis) are added to 8 ml of dry tetrahydrofuran. The tube is sealed and suspended in a silicone oil bath at 100° C. After 22 hours, the tube is allowed to cool to room temperature. The solids are dissolved in 10 ml of $CH_2Cl_2$ and 10 ml of in sodium hydroxide. The organic phase is analysed by gas chromatography and the products are isolated by column chromatography (silica gel, hexane/ethyl acetate mixtures).

Catalysts to be Used According to the Invention:

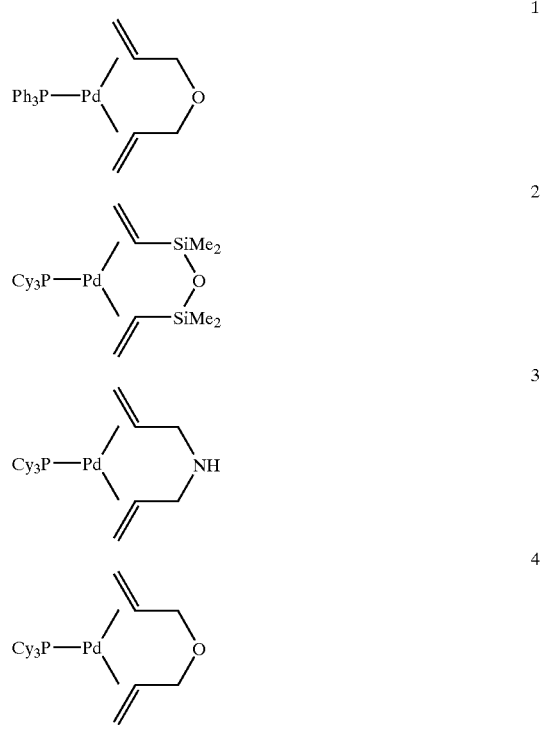

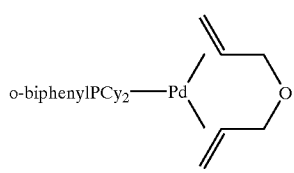

In the structural formulae of Examples 1–5:
Me represents methyl
Ph represents phenyl
Cy represents cyclohexyl
o-biphenyl represents ortho-biphenyl
Catalysts According to the Prior Art (for Comparison):
Catalyst mixture A: $Pd_2(dba)_3/PCy_3$ 1:1
Catalyst mixture B: $Pd(OAc)_2/PCy_3$ 1:1
Catalyst mixture C: $Pd(OAc)_2/PCy_3$ 1:2.
In the above:
$Pd_2(dba)_3$ represents tris-dibenzylideneacetone di-palladium(0)
$Pd(OAc)_2$ represents palladium(II) acetate
Cy represents cyclohexyl

Examples 1 to 22

Comparison of the Catalyses According to the Invention by Means of Different Substrates.[a]

TABLE 1

| No. | Haloaromatic compound*) | Product*) | Catalyst | Yield [%][b] | TON |
|---|---|---|---|---|---|
| 1 | Cl–C6H4–F | Ph–C6H4–F | 2 | 15 | 300 |
| 2 | | | 3 | 34 | 680 |
| 3 | | | 4 | 34 | 680 |
| 4 | | | 5 | 67 | 1340 |
| 5 | Cl–C6H4–OMe | Ph–C6H4–OMe | 2 | 28 | 560 |
| 6 | | | 3 | 48 | 960 |
| 7 | | | 4 | 56 | 1120 |
| 8 | | | 5 | 72 | 1440 |
| 9 | Cl–C6H4–Me | Ph–C6H4–Me | 2 | 23 | 460 |
| 10 | | | 3 | 54 | 1080 |
| 11 | | | 4 | 67 | 1340 |
| 12 | | | 5 | 82 | 1640 |
| 13 | Cl–C6H5 | Ph–C6H5 | 2 | 29 | 580 |
| 14 | | | 3 | 45 | 900 |
| 15 | | | 4 | 79 | 1580 |
| 16 | | | 5 | 87 | 1740 |

TABLE 1-continued

| No. | Haloaromatic compound*) | Product*) | Catalyst | Yield [%][b] | TON |
|---|---|---|---|---|---|
| 17 | Cl–C6H4–CN (ortho) | Ph–C6H4–CN (ortho) | 2 | 96 | 1920 |
| 18 | | | 3 | 95 | 1900 |
| 19 | | | 4 | 96 | 1920 |
| 20 | | | 5 | 97 | 1940 |
| 21 | | | 1 | 32 | 65[c] |
| 22 | | | 1 | 16 | 160[d] |

[a]0.05 mol. % catalyst.
[b]determined by gas chromatography
[c]0.5 mol. % catalyst.
[d]0.1 mol. % catalyst.
*)Ph = phenyl; Me = methyl

Examples 23 to 34

Comparison of Catalysts According to the Invention with Other Pd(0) Catalysts.[a]

TABLE 2

| No. | Haloaromatic compound*) | Product*) | Catalyst | Yield [%][b] | TON |
|---|---|---|---|---|---|
| 23 | Cl–C6H4–OMe | Ph–C6H4–OMe | A | 5 | 100 |
| 24 | | | B | 8 | 160 |
| 25 | | | C | 28 | 560 |
| 26 | | | 4 | 56 | 1120 |
| 27 | Cl–C6H5 | Ph–C6H5 | A | 8 | 160 |
| 28 | | | B | 11 | 220 |
| 29 | | | C | 28 | 560 |
| 30 | | | 4 | 79 | 1580 |
| 31 | Cl–C6H4–CN (ortho) | Ph–C6H4–CN (ortho) | A | 91 | 1820 |
| 32 | | | B | 91 | 1820 |
| 33 | | | C | 95 | 1900 |
| 34 | | | 4 | 96 | 1920 |

[a]0.05 mol. % catalyst.
[b]determined by gas chromatography
*)Ph = phenyl; Me = methyl

Examples 35 to 48

The following compounds were prepared using catalyst 4 with productivities TON greater than 5000:
35. 4-Methyl-2'-cyanobiphenyl
36. 4-Methylthio-4-fluorobiphenyl
37. 2,2'-Dimethyl-1,1'-binaphthyl
38. 2,2'-Dimethyl-6,6'-dimethoxybiphenyl
39. 4,4'-Dicyanobiphenyl
40. 3-Dimethylamino-3'-ethylbiphenyl
41. 3,5-Dimethoxy-4'-methylbiphenyl
42. 4-Trifluoromethyl-3',5'-dimethoxybiphenyl
43. 1-(N,N-Dimethylamino)-7'-bromobiphenyl
44. 2-Methoxy-2'-bromobipheyl
45. 2-Methyl-2'-bromobiphenyl
46. 1-(N,N-Dimethylamino)-1'-chlorobiphenyl
47. 2-Methoxy-2'chlorobiphenyl
48. 2-Methyl-2'-chlorobiphenyl The Examples show that with the process according to the invention it is possible in many cases to achieve yields of more than 80% with high turnover values.

Further variations and modifications of the foregoing will be apparent to those skilled in the art and are intended to be encompassed by the claims appended hereto.

German priority application 100 51 313.6 is relied on and incorporated herein by reference.

We claim:

1. A process for the preparation of a mono-, bi or poly-functional biaryl of the general formula I Ar—Ar' (I)

comprising reacting an aryl compound of formula II

Ar—X (II)

with an arylboronic acid of formula III

Ar'—B(OR$^1$)$_2$ (III)

in the presence of a catalyst,
wherein the catalyst is a metal complex of the formula IV

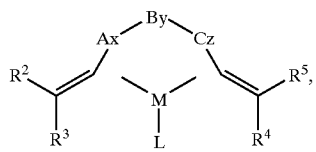
(IV)

wherein in formulae I to IV
Ar' and Ar each independently of the other represents mono- or poly-cyclic aromatic that is optionally substituted and has up to 14 carbon atoms in the ring, or heteroaromatic that is optionally substituted and has from 5 to 10 atoms in the ring, of which up to four atoms independently of one another may be N, O or S,
X represents I, Br, Cl, OSO$_2$CF$_3$, OSO$_2$(aryl), OSO$_2$(alkyl), N$_2^+$,
M represents nickel, palladium or platinum,
L represents a monodentate phosphoroorganic ligand PR$^6$R$^7$R$^8$,
A, B, C each independently of the others is a member selected from the group consisting of oxygen, sulfur, CH$_2$, C(R$^9$)$^a$(R$^{10}$)$^b$ group, N(R$^{11}$)$_c$, and Si (R$^{12}$)$^d$(R$^{13}$)$^e$ wherein a, b, c, d, e may each independently of the others be 0 or 1, and when a, b, c, d, e of at least one of said members is 0, A, B and C can also be part of a ring system,
x, y, z represent 0 or 1 and x+y+z=from 1 to 3,
R$^1$ represents hydrogen, alkyl, aryl or alkenyl, wherein in formula III B (OR$^1$)$_2$ can also form a ring system,
R$^6$ to R$^8$ have the meanings of R$^1$, or represent O-alkyl, O—C(O)-alkyl, or O-(aryl),
R$^2$ to R$^5$ and R$^9$R$^{13}$ have the meanings of R$^1$, or represent O-alkyl, O—C(O)-alkyl, O-(aryl), O—C(O)-aryl, F, Cl, OH, NO$_2$, Si(alkyl)$_3$, CF$_3$, CN, CO$_2$H, C(O)H, SO$_3$H, NH$_2$, NH(alkyl), N(alkyl)$_2$, P(alkyl)$_2$, SO$_2$(alkyl), SO(alkyl), SO(aryl), SO$_2$(aryl), SO$_3$(alkyl), SO$_3$(aryl), S-alkyl, S-aryl, S-alkenyl, NH—CO(alkyl), CO$_2$(alkyl), CONH$_2$, CO(alkyl), NHCOH, NHCO$_2$(alkyl), CO(aryl), CO$_2$(aryl), CH=CH—CO$_2$(alkyl), CH=CO—CO$_2$H, P(aryl)$_2$, PO(aryl)$_2$, PO(alkyl)$_2$, PO$_3$H and PO(O-alkyl)$_2$,
wherein alkyl represents hydrocarbon having from 1 to 10 carbon atoms and alkenyl represents mono- or poly-unsaturated hydrocarbon having from 1 to 10 carbon atoms, each of which may be branched and/or substituted by Cl, F, alkyl, O-alkyl, phenyl, O-phenyl, and aryl represents an optionally Cl-, F-, alkyl-, O-alkyl-, phenyl-, O-phenyl-substituted aromatic or heteroaromatic having from 5 to 10 atoms in the ring.

2. The process according to claim 1, wherein said aryl compound of formula II is reacted with an arylboronic acid derivative of formula III in which Ar and Ar' each independently of the other represents an optionally substituted phenyl, naphthyl, anthryl, phenanthryl or biphenyl.

3. The process according to claim 1, wherein the aryl compound of formula II is:

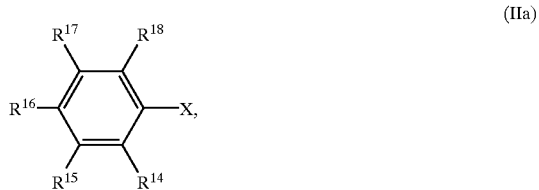
(IIa)

wherein R$^{14}$ to R$^{18}$ have the meanings given for R$^2$ to R$^5$ and R$^9$ to R$^{13}$.

4. The process according to claim 3, the arylboronic acid derivative of formula III:

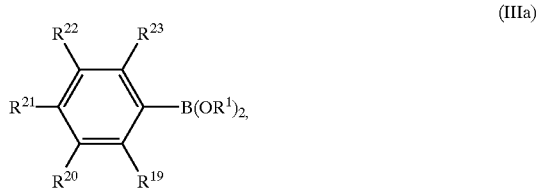
(IIIa)

wherein R$^{19}$ to R$^{23}$ have the meanings given for R$^2$ to R$^5$ and R$^9$ to R$^{13}$.

5. The process according to claim 1, wherein the catalyst of formula IV has a diene ligand which is selected from the group consisting of diallyl ether, diallylamine, diallylmethylamine, N-acetyldiallylamine, diallyl sulfide, diallylsilane, diallyldimethylsilane, divinyldisiloxane, bis-([2]thienylmethyl) ether, bis-(2-cyano-3ξξ-[2]furyl-allyl) ether, 1,1,3,3-tetramethyl-1,3-divinynl-disiloxane, difurfuryl ether, difurfurylamine, bis(thiophen-2-yl-methyl)-amine, difurfuryl sulfide, 1,1,3,3-tetramethyl-1,3-dithien-2-yldisiloxane, 1,1,3,3-tetramethoxy-1,3-divinyl-disiloxane, 1,3-dimethyl-1,3-divinyldisiloxanediol, 1,3,5,7-tetramethyl-1,3,5,7-tetravinylcyclotetra-siloxane, 1,3,5-trimethyl-1,3,5-trivinyl-cyclotrisiloxane, 1,3,5,7,9-pentamethyl-1,3,5,7,9-pentavinyl-cyclopentasiloxane, 1,3-divinylbenzene, or 2,6-divinylpyridine.

6. The process according to claim 2, wherein the catalyst of formula IV has a diene ligand which is selected from the group consisting of diallyl ether, diallylamine, diallylmethylamine, N-acetyldiallylamine, diallyl sulfide, diallylsilane, diallyldimethylsilane, divinyldisiloxane, bis-([2]thienylmethyl) ether, bis-(2-cyano-3ξξ-[2]furyl-allyl) ether, 1,1,3,3-tetramethyl-1,3-divinyl-disiloxane, difurfuryl ether, difurfurylamine, bis(thiophen-2-yl-methyl)-amine, difurfuryl sulfide, 1,1,3,3-tetramethyl-1,3-dithien-2-yldisiloxane, 1,1,3,3-tetramethoxy-1,3-divinyl-disiloxane, 1,3-dimethyl-1,3-divinyldisiloxanediol, 1,3,5,7-tetramethyl- 1,3,5,7-tetravinylcyclotetra-siloxane, 1,3,5-trimethyl-1,3,5-trivinyl-cyclotrisiloxane, 1,3,5,7,9-pentamethyl-1,3,5,7,9-pentavinyl-cyclopentasiloxane, 1,3-divinylbenzene, or 2,6-divinylpyridine.

7. The process according to claim 3, wherein the catalyst of formula IV has a diene ligand which is selected from the group consisting of diallyl ether, diallylamine, diallylmethylamine, N-acetyldiallylamine, diallyl sulfide, diallylsilane, diallyldimethylsilane, divinyldisiloxane, bis-([2]thienylmethyl) ether, bis-(2-cyano-3ξξ-[2]furyl-allyl) ether, 1,1,3,3-tetramethyl-1,3-divinyl-disiloxane, difurfuryl ether, difurfurylamine, bis(thiophen-2-yl-methyl)-amine, difurfuryl sulfide, 1,1,3,3-tetramethyl-1,3-dithien-2-yldisiloxane, 1,1,3,3-tetramethoxy-1,3-divinyl-disiloxane, 1,3-dimethyl-1,3-divinyldisiloxanediol, 1,3,5,7-tetramethyl-1,3,5,7-tetravinylcyclotetra-siloxane, 1,3,5-trimethyl-1,3,5-trivinyl-cyclotrisiloxane, 1,3,5,7,9-pentamethyl-1,3,5,7,9-pentavinyl-cyclopentasiloxane, 1,3-divinylbenzene, or 2,6-divinylpyridine.

8. Process according to claim 4, wherein the catalyst of formula IV has a diene ligand which is selected from the group consisting of diallyl ether, diallylamine, diallylmethylamine, N-acetyldiallylamine, diallyl sulfide, diallylsilane, diallyldimethylsilane, divinyldisiloxane, bis-([2]thienylmethyl) ether, bis-(2-cyano-3ξξ-[2]furyl-allyl) ether, 1,1,3,3-tetramethyl-1,3-divinynl-disiloxane, difurfliryl ether, difurfurylamine, bis(thiophen-2-yl-methyl)-amine, difurfuryl sulfide, 1,1,3,3-tetramethyl-1,3-dithien-2-yldisiloxane, 1,1,3,3-tetramethoxy-1,3-divinyl-disiloxane, 1,3-dimethyl-1,3-divinyldisiloxanediol, 1,3,5,7-tetramethyl-1,3,5,7-tetravinylcyclotetra-siloxane, 1,3,5-trimethyl-1,3,5-trivinyl-cyclotrisiloxane, 1,3,5,7,9-pentamethyl-1,3,5,7,9-pentavinyl-cyclopentasiloxane, 1,3-divinylbenzene, or 2,6-divinylpyridine.

9. The process according to claim 1, wherein the the catalyst of formula IV has a ligand L which is a trialkylphosphine or a triarylphosphine in which alkyl and aryl have the meanings defined.

10. The process according to claim 9, wherein the catalyst of formula IV ligand L which is tricyclohexylphosphine, tri-tert-butylphosphine, triphenylphosphine, tri-o-tolylphosphine, di-(1-adamantyl)-n-butylphosphine, di-(1-adamantyl)-isopropyl-phosphine, di-(1-adamantyl)-cyclohexylphosphine, 2-(di-cyclohexylphosphino)-biphenyl, 2-(dicyclohexyl-phosphino)-toluene, N,N-dimethyl-2-(dicyclohexyl-phosphino)-aniline, 2-(di-tert-butylphosphino)-biphenyl, 2-(di-tert-butyl-phosphino)-toluene, N,N-dimethyl-2-(di-tert-butylphosphino)-aniline.

11. The process according to claim 1, wherein the catalyst is present in an amount from 0.001 to 10 mol. %, based on the concentration of aryl compound or arylboronic acid.

12. The process according to claim 1, wherein the catalyst is present in an amount from 0.01 to 1 mol. % based on the concentration of aryl compound or arylboronic acid.

13. The process according to claim 1, further comprising reacting at temperatures of from 0 to 200° C.

14. The process according to claim 1, further comprising reacting at temperatures of from 40 to 180° C.

15. The process according to claim 1, further comprising reacting at temperatures of from 60 to 160° C.

16. The process according to claims 1, further comprising carrying the reaction out at a pressure of from 0.5 to 100 bar.

17. The process according to claim 1, further comprising adding a base.

18. The process according to claim 17, wherein the base is a primary, secondary or tertiary amine.

19. The process according to claim 17, wherein the base is a alkylamine, dialkylamine or trialkylamine.

20. The process according to claim 17, wherein the base is an alicyclic or open chain amine.

21. The process according to claim 17, wherein the base is an alkali metal or alkaline earth metal salt of aliphatic or aromatic carboxylic acids.

22. The process according to claim 17, wherein the base is an acetate, propionate, benzoate, or an alkali metal or alkaline earth metal carbonate, hydrogen carbonate, phosphate, hydrogen phosphate, oxide or hydroxide.

23. The process according to claim 17, wherein the base is a metal alkoxide.

24. The process according to claim 17, wherein the base is a sodium methanolate, potassium methanolate, potassium ethanolate, magnesium ethanolate, calcium ethanolate, calcium methanolate, sodium ethanolate, magnesium methanolate, sodium tert-butanolate or potassium tert-butanolate.

25. The process according to claim 1, further comprising adding a co-catalyst.

26. The process according to claim 25, wherein the co-catalyst is the salt of a halogen.

27. The process according to claim 25, wherein the co-catalyst is a halide of the alkali metal or alkaline earth metal elements, an ammonium halide, a tetraalkylammonium halide, a phosphonium halide or a tetraalkylphosphonium halide.

28. The process according to claim 25, wherein the co-catalyst is a fluoride, bromide or chloride.

29. The process according to claim 25, wherein the co-catalyst is a lithium bromide, lithium chloride, sodium bromide, potassium bromide, cesium bromide, tetrabutylammonium chloride, tetrabutylammonium fluoride, cesium fluoride, calcium fluoride, sodium fluoride, potassium fluoride, tetrabutylammonium fluoride, benzyltrimethylammonium bromide, benzyltrimethylammonium chloride, tetraphenylphosphonium bromide, tetraphenylphosphonium chloride, or trioctylmethylammonium bromide.

30. The process according to claim 25 wherein the co-catalyst is added in an amount of from 0.01 to 500 mol. %, based on the amount of aryl compound or arylboronic acid.

31. The process according to claim 25 wherein the co-catalyst is added in an amount of from 0.1 to 300 mol. %, based on the amount of aryl compound or arylboronic acid.

32. The process according to claim 26 wherein the co-catalyst is added in an amount of from 0.01 to 500 mol. %, based on the amount of aryl compound or arylboronic acid.

33. The process according to claim 26 wherein the co-catalyst is added in an amount of from 0.1 to 300 mol. %, based on the amount of aryl compound or arylboronic acid derivative.

34. Process according to claim 1, wherein the catalyst of formula IV is prepared in situ.

35. The process according to claim 23, wherein the metal alkoxide is an alkaline earth metal alkoxide.

* * * * *